US00PP08751P

United States Patent [19]

Hanes

[11] Patent Number: Plant 8,751

[45] Date of Patent: May 24, 1994

[54] GERANIUM NAMED ECLIPSE WHITE

[75] Inventor: Mitchell Hanes, Morgan Hill, Calif.

[73] Assignee: Goldsmith Seeds, Inc., Gilroy, Calif.

[21] Appl. No.: 50,501

[22] Filed: Apr. 20, 1993

[51] Int. Cl.[5] ..... A01H 5/00

[52] U.S. Cl. ..... Plt./87.12

[58] Field of Search ..... Plt. 87.12

*Primary Examiner*—James R. Feyrer

*Attorney, Agent, or Firm*—Tilton, Fallon, Lungmus & Chestnut

[57] ABSTRACT

A new geranium cultivar particularly distinguished by its large white semi-double flowers, and its dark green foliage with slight zonation. The plant itself is strong and vigorous, especially for a dark leafed variety, and grows to a height of 15–20 cm. as a 5½ inch potted plant.

1 Drawing Sheet

BACKGROUND OF THE NEW PLANT

The present invention comprises a new and distinct tetraploid cultivar of geranium, botanically known as *Pelargonium hortorum* Bailey. The new cultivar is propagated from a seedling resulting from the cross of two tetraploid, unreleased, proprietary, inbred lines: a white-colored, single flowered, dark leaf seed parent developed in our breeding program, known as plant 1475-1 and a white-colored semi-double flowered pollen parent known as 1560-3.

This new plant is a product of a planned breeding program intended to create new geranium cultivars with white colored semi-double flowers, dark green foliage, with strong growth habits and good cutting productivity.

The new cultivar was created in 1990 in Gilroy, Calif. and has been repeatedly asexually reproduced by cuttings in Gilroy, Calif. and Guatemala over a three year period. It has also been trialed at Akemos, Mich. It has been found to retain its distinctive characteristics through successive propagations; and this novelty appears to be firmly fixed.

DESCRIPTION OF THE DRAWING

This new geranium plant is illustrated by the accompanying photographic drawing which shows blooms, buds, and foliage of the plant in full color, the color shown being as true as can be reasonably obtained by conventional photographic procedures.

DESCRIPTION OF THE NEW CULTIVAR

The following detailed descriptions set forth the distinctive characteristics of this new geranium. The data which defines these characteristics was collected from asexual reproductions carried out in Gilroy, Calif. The plant history was taken on 20 week old plants, blossomed under natural light in a greenhouse. Color readings were taken in the greenhouse on Mar. 1, 1993 under ambient light. Color references are primarily to the R.H.S. Colour Chart of the Royal Horticultural Society of London.

THE PLANT

Classification:

*Botanical.*—*Pelargonium hortorum* Bailey.

*Commercial.*—Zonal geranium.

Form: Compact, basal branching with a dense canopy.

Height: 15 to 20 cm. as a 5½ inch potted plant, excluding blooms.

Growth: Vigorous, especially for a dark leaf variety.

Internode: Approximately 1.5 cm. in length.

Strength: Very good cutting producer, and the plant performs very well after shipping as a rooted or unrooted cutting. Cuttings are fast to root.

Foliage: Abundant quantity.

*Leaves.*—Normal shape, dark color.

*Size.*—Diameter about 10–13 cm.

*Shape.*—Rounded cordate with occasional upfolding between veins.

*Margin.*—Irregularly crenate.

*Texture.*—Leathery and pubescent on both surfaces, especially along veins.

*Ribs and veins.*—Distinctly palmate, 4 to 8 cm. long.

*Color.*—Upper side: Dark green with very slight green shadowy zonation extending inward 3 cm. from leaf edge. Under side: Lighter green color. Ribs and veins not prominently different from the upper surface.

Petioles: About 7 to 12 cm. in length.

THE BUD

Size:

*Diameter.*—About 4 mm.

*Length.*—About 2.0 to 3.0 cm. at the time of bud opening.

Shape: Pointed ovoid.

Color: Of petals when sepals first divide, RHS 155-D.

Sepals: Five in number, flat behind petals, pointed linear lanceolate, lettuce green RHS 144-A in an open flower.

THE FLOWER

Blooming habit: Continuous throughout the year when grown in a frost free environment.

Size: Approximately 3.8 cm. in diameter, 1.5 cm. deep, irregularly radially symmetrical.

Form: Cup-shaped when bloom first opens, later flattening to shallow cup shape with maturity.

Petals: Five imbricate outer petals, 1.7–1.9 cm. wide and approximately 2.3 cm. long. Three to five inner smaller petaloids of varying shape. Both the outer petals and inner petaloids are white, RHS 155-D. Color changing little with age. Petals and petaloids are soft and satiny.

Pedicel: Approximately 2.3 cm. in length.

Persistence: Nonshattering flower. Removal of spent flowers grooms the plant but is not necessary to maintain continuous flowering.

INFLORESCENCE

Type: An umbel composed of approximately 25 flowers, erect or laterally ascending, with a maximum diameter of about 11 cm. On a 12 week old plant in a 6 inch pot typically there will be 2–3 umbels.

Peduncle: Approximately 7–12 cm. in length, usually 10 cm., green in color.

REPRODUCTIVE ORGANS

Stamens:

*Anthers.*—Five to eight positioned below the mature stigma, dull red prior to anthesis.

*Filaments.*—White through the entire length.

*Pollen.*—Orange in color.

Pistil:

*Number.*—One.

*Length.*—Approximately 6 mm.

*Stigma.*—Five linear lobes of near equal length, curling back toward the ovary, white in color.

*Style.*—Normal for species. Length: About 2.5–3.5 mm. Color: White.

Ovaries: Light green at anthesis, densely pubescent with white hairs, oblong. Green drying to a light brown at maturity.

Fruit: Partially fertile.

I claim:

1. A new and distinct geranium cultivar substantially as herein shown and described, characterized by its white colored, semi-double flowers on large umbels, dark green foliage with faint zonation; the plant being fast rooting and having a vigorous compact growth habit.

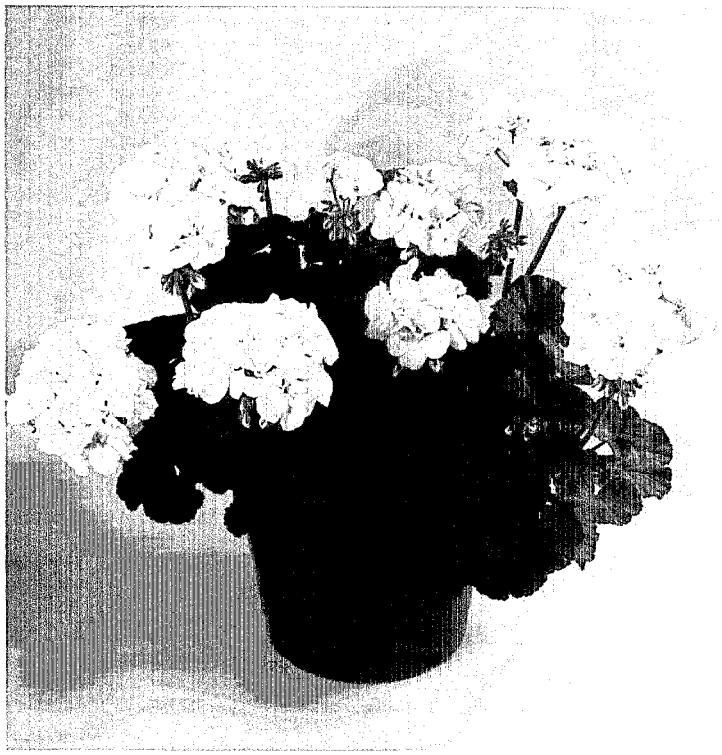

* * * * *